United States Patent
Grundei

(10) Patent No.: US 8,226,731 B2
(45) Date of Patent: Jul. 24, 2012

(54) CONNECTION ADAPTER

(75) Inventor: Hans Grundei, Lübeck (DE)

(73) Assignee: Orthodynamics GmbH, Lubeck (DE)

( * ) Notice: Subject to any disclaimer, the term of this patent is extended or adjusted under 35 U.S.C. 154(b) by 39 days.

(21) Appl. No.: 12/936,293

(22) PCT Filed: Jan. 19, 2009

(86) PCT No.: PCT/EP2009/050552
§ 371 (c)(1),
(2), (4) Date: Dec. 10, 2010

(87) PCT Pub. No.: WO2009/121636
PCT Pub. Date: Oct. 8, 2009

(65) Prior Publication Data
US 2011/0190906 A1    Aug. 4, 2011

(30) Foreign Application Priority Data

Apr. 3, 2008 (DE) .......................... 10 2008 000 977

(51) Int. Cl.
*A61F 2/60* (2006.01)
*A61F 2/78* (2006.01)
(52) U.S. Cl. ........................................ 623/32
(58) Field of Classification Search ............ 623/27, 623/28, 32
See application file for complete search history.

(56) References Cited

U.S. PATENT DOCUMENTS

| | | | | |
|---|---|---|---|---|
| 3,947,897 A | * | 4/1976 | Owens | ........................ 623/11.11 |
| 2008/0058957 A1 | * | 3/2008 | Newcombe et al. | ............ 623/32 |

FOREIGN PATENT DOCUMENTS

| | | |
|---|---|---|
| DE | 9 826 638 | 7/2000 |
| EP | 1 309 297 | 11/2005 |
| GB | 2 411 841 | 9/2005 |
| WO | WO2007/018904 | 2/2007 |

* cited by examiner

*Primary Examiner* — Bruce E Snow
(74) *Attorney, Agent, or Firm* — Alix, Yale & Ristas, LLP

(57) ABSTRACT

A connection adapter between a rigid transcutaneous implant can be anchored intracorporeally in a femoral stump, and a part of an extracorporeal orthopaedic knee joint. The connection adapter comprises a first coupling part for connection to the transcutaneous implant and a second coupling part for connection to the knee joint. The second coupling can be connected releasably to the first coupling part. A safety coupling is arranged in the interior of the second coupling part and transfers a torsional moment between the first coupling part and the second coupling part and slips through when an adjustable maximum value of the torsional moment is exceeded.

20 Claims, 2 Drawing Sheets

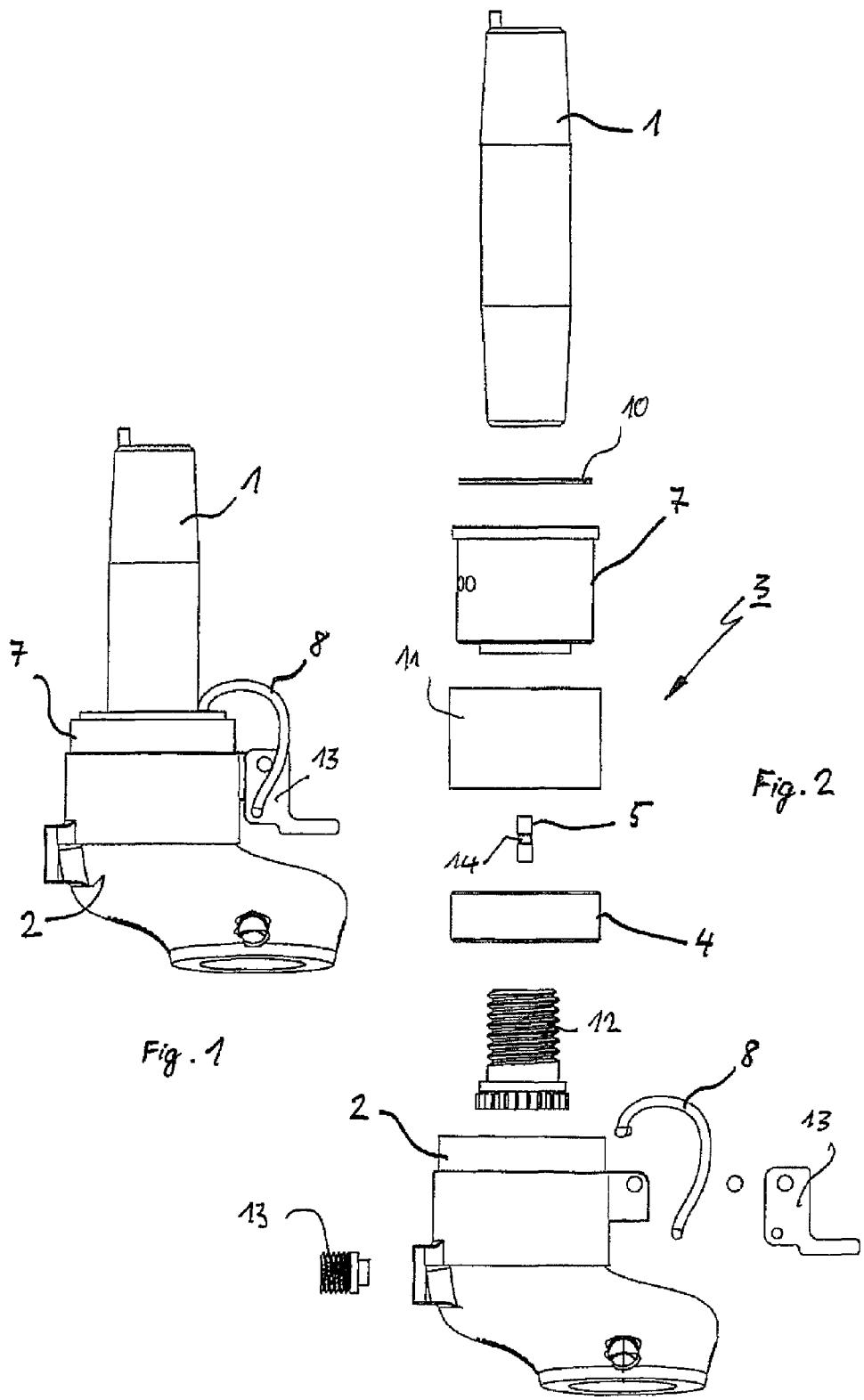

CONNECTION ADAPTER

This application is the National Stage filing of PCT/EP2009/050552, filed 19 Jan. 2009, which claims priority to German application No. 10 2008 000 977.6, filed 3 Apr. 2008.

BACKGROUND

The present invention relates to a connection adapter between a rigid transcutaneous implant, which can be anchored intracorporeally in a femoral stump, and a part of an extracorporeal orthopedic knee joint.

A transcutaneous implant of this type is known from DE 198 26 638 C2. The adapter disclosed therein for an exoprosthetic standard part can be seated with a proximal stem part in a tubular bone stump, the stem part being covered at least partly by an open-meshed, three-dimensional spatial network structure and being provided at its distal end with a coupling device for the exoprosthetic standard part. The open-meshed, three-dimensional spatial network structure, which is also referred to as interconnecting, makes it possible for natural bone material to grow in, through, behind and around it during the healing phase in such a way that the stem part is integrated into the tubular bone, in any case with respect to the substrate flow, within a relatively short period of time, and an extremely stable secondary fixation is ensured. The distal end of the implant exits from the stump of the limb and provides a coupling option for an exoprosthetic standard part, for example an extracorporeal orthopedic joint.

The immediate perception thus obtained of external skeletal loading of the patient is referred to as osseoperception. This affords the patient, for example a thigh amputee, a completely different type of perception.

The connection between the adapter and the natural bone can, however, turn out to be so strong that even this desired strength can lead to problems, namely if there is extreme exposure to forces. From the outset it cannot therefore be ruled out that an extreme, for example shear, loading of the artificial knee joint or a loading of the lower-limb prosthesis will be transferred into the intramedullary anchored adapter in the femoral stump where it may lead to fracturing. For this purpose it was proposed in EP 1 309 297 B1 to form a leg prosthesis of this type in such a way that it comprises a predetermined breaking point arranged extracorporeally that permits the prosthesis part to break off upon application of a force of predetermined magnitude. This type of described predetermined breaking point is intended to break in the event of a torsional or tilting moment.

However, any torsional moments applied about the femur-tibia axis are even more critical. If excessive torsional moments are applied, this may lead to a spiral fracture above the implant anchored in the femoral stump. Torsional moments of this type may ultimately lead to fractures of the femoral neck.

This should naturally be avoided. A connection adapter of the above-mentioned type is developed in such a way that, where possible, torsional moments applied about the femur-tibia axis no longer lead to spiral fractures in the femoral stump.

SUMMARY

A connection adapter of the above-mentioned type, in which a releasing safety coupling arranged inside the second coupling part is provided, transfers a torsional moment between the first coupling part and the second coupling part and slides through when an adjustable maximum value of the torsional moment is exceeded. In this context, a releasing safety coupling is to be understood as a safety coupling that can only be brought manually back into the state in which it can carry out its intended function once activated, i.e., once the cooperation between the first and second coupling parts has been broken.

If the torsional moment exceeds the aforementioned maximum value, then the coupling (as described) lips through, i.e., the exoprosthesis below the connection adapter can rotate about its axis whereby the high torsional moment is not transferred into the femoral stump and the risk of spiral fractures is eradicated. In this instance, the connection adapter is brought back into the starting position using simple handles in such a way that high costs are not incurred.

The maximum value of the torsional moment is preferably adjustable in the range from 5 to 35 Nm. This corresponds approximately to stresses that may be produced in a patient weighing 70 to 130 kg.

In a particularly preferred embodiment the aforementioned safety coupling is formed of a torsion disc fixed in the second coupling part, from which torsion disc at least one shearing pin extends and engages with corresponding sockets in an end face of a sleeve that is, in turn, connectable to the first coupling part.

The main function of the safety coupling is undertaken by the at least one shearing pin. This pin is formed in such a way that it shears off once the maximum value of the torsional moment has been exceeded so there is no longer a positive and non-positive connection between the first and second coupling parts. In other words, the shearing pin is sheared off once the calculated maximum value of the torsional moment has been exceeded, and the exoprosthesis arranged beneath the connection adapter can be rotated about its axis without causing any further damage.

The design is advantageously conceived in such a way that the torsional moment is transferable without play up to the maximum value. In other words, an optimal non-positive and positive connection is ensured between the shearing pin, the torsion disc and the aforementioned sleeve.

The maximum value of the torsional moment to be transferred is adjustable via the selection of material, shape or arrangement of a plurality of shearing pins.

The shearing pins may therefore preferably comprise slightly deformable material, such as copper or brass. With regard to the possibility of adjusting the maximum value of the torsional moment to be transferred, reference should be made to the particularly preferred embodiment in which a plurality of shearing pins are provided with notches of different depths.

With regard to the possibility of adjusting the maximum value of the torsional moment to be transferred by the arrangement of a plurality of shearing pins, it is worth mentioning the embodiment in which a plurality of shearing pins are arranged on segments of a circle on the torsion disc. The corresponding sockets in the end face of the sleeve are arranged accordingly.

An embodiment in which the at least one shearing pin is replaceable with another is particularly preferred. This feature is of great importance once the maximum value of the torsional moment to be transferred has been exceeded and the shearing pin(s) has/have been sheared off. The replaceability of the shearing pins actually makes it possible to open the connection adapter, remove the sheared-off shearing pins and replace them with new shearing pins. The costs associated with replacement of the shearing pins are limited, i.e., it is not a complete disaster if the safety coupling is disengaged as intended.

A preferred development provides for a tensible tension spring to be articulated to the second coupling part, to ensure that the components are held together when tensioned and to transfer the torsional moment without play by pressing the sleeve against the torsion disc, while enclosing the at least one shearing pin. The clamping force of the tension spring ensures the correct above-mentioned non-positive and positive connection between the shearing pins and the torsion disc on the one hand, and between the shearing pins and the sleeve on the other hand. At the same time, the tension spring is an element that can be detached easily in order to replace the shearing pins where necessary. The tension spring is particularly preferably configured as a clamp clip.

An embodiment in which the first coupling part is a double cone and the sleeve is a conical sleeve has also proven to be particularly effective. This embodiment ensures a high degree of stability of the connections whilst simultaneously providing simple detachability of the parts for possible inspection.

BRIEF DESCRIPTION OF THE DRAWINGS

The invention will now be described in greater detail with reference to an embodiment according to the drawings, in which:

FIG. 1 is a side view of the connection adapter;

FIG. 2 is an exploded view of the connection adapter according to FIG. 1;

DETAILED DESCRIPTION

Figure 3:
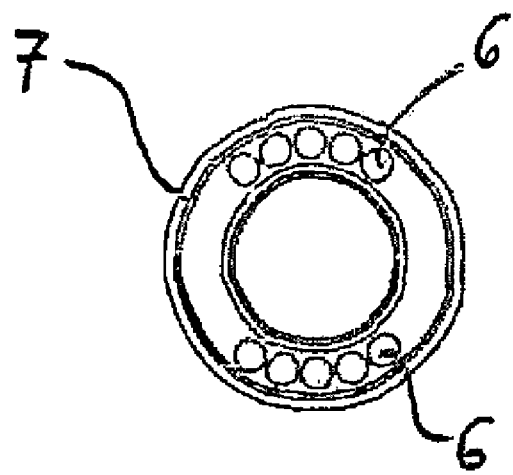
FIG. 3 shows the lower end face of the sleeve of the adapter.

Like parts are provided with like reference numerals in the following.

FIG. 1 gives a first overview. It shows a side view of the connection adapter.

The adapter comprises a first coupling part 1 in the form of a double cone. It produces a connection to the transcutaneous implant (not shown) whereas the lower cone of the double cone 1 produces a connection to a cone sleeve 7. The double cone 1 passes through a silicone ring 10.

The second coupling part 2 connects to an extracorporeal orthopedic knee joint (not shown in the present case).

The conical sleeve 7 plugs into a rotary sleeve 11. At least one shearing pin 5 produces a connection to a torsion disc 4. By contrast, the torsion disc 4 is fixed in the second coupling part 2.

A self-locking safety screw 12 passes through the torsion disc and locks the conical press fit of the double cone 1 in the conical sleeve 7. A safety set screw 13 is provided to prevent loosening of the torsion disc 4. The parts are held together by a tension spring in the form of a clamp clip 8 that is articulated at the second coupling part 2 via a bearing block 13. The clamp clip 8 presses against the silicone ring 10 and also against the sleeve 7 in such a way that the parts adopt a stable connection.

Figure 4:
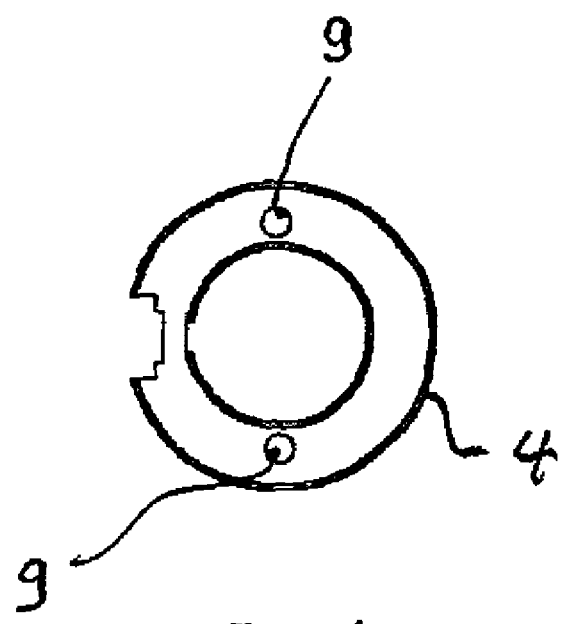
FIG. 4 shows the upper face of the torsion disc of the adapter.

The core of the connection adapter is the safety coupling 3, which is formed in particular of the following parts: torsion disc 4, shearing pin 5 and sleeve 7. Reference is made to FIGS. 3 and 4 for comprehension of this.

FIG. 3 shows the lower end face of the sleeve 7. A row of recesses or holes 6 arranged on a segment of a circle can be seen. These are dimensioned in such a way that the shearing pin(s) 5 can be received therein with a positive fit.

The counter piece to this is the torsion disc 4, the upper face of which is shown in FIG. 4. In this instance, two recesses 9 can be seen, into each of which a shearing pin 5 can be placed with a positive fit. A torsional movement about the vertical axis of the connection adapter, i.e., about the longitudinal axis of the double cone 1, is thus transferred to the sleeve 7 by the torsion disc 4 via the shearing pins 5. The shearing pin 5 is provided with a notch 14, the configuration of which can define the breaking point of the pin, i.e., the point from where the shearing pin 5 is sheared off at a specific torsional moment. Once the shearing pin has sheared off, it is no longer possible for the torsional moment to be transferred from the second coupling part to the first coupling part. Instead, the second coupling part (and therefore the artificial knee joint) can rotate on the conical sleeve 7 by means of the rotary sleeve 11.

If shearing pins 5 are sheared off, the connection adapter can easily be produced again by opening the clamp clip 8 and removing the sheared off shearing pins. These are then replaced by new shearing pins and the connection adapter is closed again by clamping the clamp clip.

The invention claimed is:

1. Connection adapter between a rigid transcutaneous implant, which can be anchored intracorporeally in a femoral stump, and a part of an extracorporeal orthopaedic knee joint, said connection adapter comprising a first coupling part for connection to the transcutaneous implant and a second coupling part for connection to the knee joint, the second coupling part being releasably connectable to the first coupling part characterized by a releasing safety coupling which is arranged inside the second coupling part, transfers a torsional moment between the first coupling part and the second coupling part, slides through when an adjustable maximum value of the torsional moment is exceeded, and is formed of a torsion disc fixed in the second coupling part from which torsion disc at least one shearing pin extends and engages with corresponding sockets in an end face of a sleeve that is in turn connectable to the first coupling part.

2. Connection adapter according to claim 1, wherein the maximum value of the torsional moment is adjustable in the range from 5 to 35 Nm.

3. Connection adapter according to claim 1, wherein the torsional moment is transferable without play up to the maximum value.

4. Connection adapter according to claim 1, wherein the maximum value of the torsional moment to be transferred is adjustable via the selection of material, shape or arrangement of a plurality of shearing pins.

5. Connection adapter according to claim 1, wherein the shearing pins consist of slightly deformable material.

6. Connection adapter according to claim 5, wherein the material is copper.

7. Connection adapter according to claim 5, wherein the material is brass.

8. Connection adapter according to claim 4, wherein a plurality of shearing pins are provided with notches of different depths.

9. Connection adapter according to claim 4, wherein a plurality of shearing pins are arranged on segments of a circle on the torsion disc.

10. Connection adapter according to claim 1, wherein the at least one shearing pin is replaceable with another.

11. Connection adapter according to claim 1, wherein a tensible tension spring is articulated to the second coupling part, ensures that the components are held together when tensioned and transfers the torsional moment without play by pressing the sleeve against the torsion disc, while enclosing the at least one shearing pin.

12. Connection adapter according to claim 11, wherein the tension spring is configured as a clamp clip.

13. Connection adapter according to claim 1, wherein the first coupling part is a double cone and the sleeve is a conical sleeve.

14. Connection adapter according to claim 2, wherein the torsional moment is transferable without play up to the maximum value.

15. Connection adapter according to claim 5, wherein a plurality of shearing pins are provided with notches of different depths.

16. Connection adapter according to claim 6, wherein a plurality of shearing pins are provided with notches of different depths.

17. Connection adapter according to claim 7, wherein a plurality of shearing pins are provided with notches of different depths.

18. Connection adapter according to claim 5, wherein a tensible tension spring is articulated to the second coupling part, ensures that the components are held together when tensioned and transfers the torsional moment without play by pressing the sleeve against the torsion disc, while enclosing the at least one shearing pin.

19. Connection adapter according to claim 6, wherein a tensible tension spring is articulated to the second coupling part, ensures that the components are held together when tensioned and transfers the torsional moment without play by pressing the sleeve against the torsion disc, while enclosing the at least one shearing pin.

20. Connection adapter according to claim 7, wherein a tensible tension spring is articulated to the second coupling part, ensures that the components are held together when tensioned and transfers the torsional moment without play by pressing the sleeve against the torsion disc, while enclosing the at least one shearing pin.

\* \* \* \* \*